US011579233B2

(12) United States Patent
Wang et al.

(10) Patent No.: US 11,579,233 B2
(45) Date of Patent: Feb. 14, 2023

(54) METHOD FOR OPTIMIZING THE ORIENTATION PERFORMANCE OF RADIATION SOURCE ORIENTATION SYSTEM

(71) Applicants: Chengdu University of Information Technology, Chengdu (CN); Shoude Wang, Guiyang (CN)

(72) Inventors: Jiang Wang, Chengdu (CN); Juan Wu, Chengdu (CN); Jianxin He, Chengdu (CN); Yuming Du, Chengdu (CN); Xinggang Zhang, Chengdu (CN); Shoude Wang, Guiyang (CN)

(73) Assignees: Chengdu University of Information Technology, Chengdu (CN); Wang Shoude, Guiyang (CN)

( * ) Notice: Subject to any disclaimer, the term of this patent is extended or adjusted under 35 U.S.C. 154(b) by 359 days.

(21) Appl. No.: 16/883,854

(22) Filed: May 26, 2020

(65) Prior Publication Data
US 2020/0379077 A1   Dec. 3, 2020

(51) Int. Cl.
*G01S 3/00*   (2006.01)
*A61B 6/00*   (2006.01)

(52) U.S. Cl.
CPC .. *G01S 3/00* (2013.01); *A61B 6/00* (2013.01)

(58) Field of Classification Search
CPC .................................... G01S 3/00; A61B 6/00
See application file for complete search history.

(56) References Cited

U.S. PATENT DOCUMENTS

2013/0116561 A1* 5/2013 Rothberg ................. A61B 8/56
                                                                          600/459

FOREIGN PATENT DOCUMENTS

| CN | 101907457 A |   | 7/2010 |
|---|---|---|---|
| CN | 102798374 A |   | 7/2012 |
| CN | 102798374 A | * | 11/2012 |
| CN | 108181606 A |   | 12/2017 |

* cited by examiner

*Primary Examiner* — Peter M Bythrow
*Assistant Examiner* — Nazra Nur Waheed
(74) *Attorney, Agent, or Firm* — Elliott, Ostrander & Preston, P.C.

(57) ABSTRACT

The present invention relates to a radiation source orientation technology. The invention discloses a method for optimizing the orientation performance of radiation source orientation system, which comprises the following steps: establishing a radiation source orientation matrix; obtaining the non-zero singular value of the orientation matrix; classifying orientation noise that affects the radiation source orientation system according to the distribution characteristic of noise energy; determining the optimal orientation matrix of the radiation source orientation system according to the minimum non-zero singular value $\sigma_{min}$ of the orientation matrix and its number of array elements m; determining the optimal orientation array according to the non-zero singular value of orientation matrix considering the distribution of different noise energy. The invention lays a foundation for the optimal design of a non-planar array in a radiation source orientation system. The optimal orientation matrix and array provided by the invention can be used to effectively improve the orientation accuracy of the radiation source orientation system and the resistance of the orientation system to interference.

12 Claims, 2 Drawing Sheets

METHOD FOR OPTIMIZING THE ORIENTATION PERFORMANCE OF RADIATION SOURCE ORIENTATION SYSTEM

This is a U.S. national-phase patent application filed under 35 U.S.C. § 119, claiming priority to Chinese patent application no. CN201910461991.6 filed 30 May 2019.

FIELD OF THE INVENTION

The invention relates to the technical field of radiation source orientation, particularly to a method for optimizing the performance of radiation source orientation system, and specifically to a method for optimizing orientation matrix and orientation array of the radiation source orientation system.

BACKGROUND OF THE INVENTION

Radiation sources, including optical radiation source, electromagnetic wave radiation source and radioactive radiation source, can radiate energy outwards. The radiation source orientation determination technology is used for observing the orientation of space radiation sources.

The passive orientation determination technology of radiation source plays an important role in civil and military applications such as navigation, aerospace, electronic warfare and so on. The orientation determination technology based on radiation energy is a significant component of passive orientation determination technologies for radiation sources. This technology measures the basic feature of radiation sources—radiation energy, which theoretically meets the passive orientation determination of all radiation sources. Therefore, it has great advantages in the application range. Moreover, the orientation determination technology only requires that the ratio of the energy radiated by the radiation source on the array element to the measured value is a constant, and it is relatively simple to measure the radiant energy, so it has advantages in the system implementation.

The radiation source orientation determination based on the energy of non-planar array elements is a method using radiation energy to determine radiation source orientation. The method is to obtain the space angle, azimuth angle and zenith angle, of the radiation source by solving the radiation source orientation equation, which is formed by unit normal vectors of mounting plane of array elements on a non-planar array (e.g., a polyhedron array) and the measured radiation energy on array elements. Chinese patents No. CN101907457A, CN102798374A and CN108181606 disclose such radiation source orientation technology.

In applications, the orientation noise caused by the interference of system internal and environmental interference is inevitable. Usually the radiation source vector, which is composed of unknown variables of the radiation source orientation equation, cannot be directly calculated through the orientation equation. Therefore, it was first proposed to use the ordinary least square (OLS) solution of the radiation source orientation equation to estimate the radiation source vector. Subsequently, the algorithm to compensate the orientation noise caused by the system internal interference and the method for optimizing the non-planar array structure were also proposed in order to improve the orientation accuracy of the radiation source. However, in-depth research on the OLS orientation performance was rarely reported in the prior art, especially no relevant research has been achieved in terms of method to optimize the radiation source orientation matrix and orientation array, which to a great extent hinders the optimization and improvement of radiation source orientation performance.

SUMMARY OF THE INVENTION

The purpose of the invention is to provide a method for optimizing the radiation source orientation matrix and orientation array, and a basis for optimizing the orientation performance of radiation source orientation system.

To achieve the above purpose, one aspect of the embodiment of the invention provides a method for optimizing the orientation performance of radiation source orientation system, characterized by comprising the following steps:

Establishing the radiation source orientation matrix;

Obtaining the non-zero singular value of the orientation matrix;

Classifying orientation noise that affects the radiation source orientation system according to the distribution characteristic of noise energy;

Determining the optimal orientation matrix of the radiation source orientation system according to the minimum non-zero singular value $\tau_{min}$ of the orientation matrix and its number of array elements m;

Determining the optimal orientation array is according to the non-zero singular value of orientation matrix considering different noise energy distribution.

Further, in case of energy bounded orientation noise, among all the orientation matrices of the radiation source orientation system, the orientation matrix with the largest minimum non-zero singular value $\tau_{min}$ should be taken as the optimal orientation matrix.

Further, in case of energy unbounded orientation noise, among all the orientation matrices of the radiation source orientation system, the matrix with the smallest $\sqrt{m}/\sigma_{min}$ should be taken as the optimal orientation matrix.

Further, in case of energy bounded orientation noise and energy unbounded orientation noise existing at the same time, the orientation matrix with the smallest interference factor $\kappa$ and the smallest average interference factor $k_a$ should be taken as the optimal orientation matrix;

where, $k=1/\sigma_{min}$, $k_a=\sqrt{m}/\sigma_{min}$; m is the number of array elements constituting the orientation matrix, $m \geq 3$.

Further, in case of energy bounded orientation noise, all array elements of the optimal orientation array are radiated by the radiation source on a given detection field. The minimum non-zero singular value $\sigma_{min}$ of the orientation matrix comprising all array elements of the optimal orientation array satisfies the relational expression:

$$\sigma_{min} = \sqrt{m/3};$$

where, m is the number of array elements constituting the orientation matrix, $m \geq 3$.

Further, in case of energy unbounded orientation noise, among all the orientation matrices comprising the radiated array elements under the optimal orientation array, there should be at least one orientation matrix with the minimum non-zero singular value $\sigma_{min}$ satisfying the relational expression:

$$\sigma_{min} = \sqrt{m/3};$$

where, m is the number of array elements constituting the orientation matrix, $m \geq 3$.

Further, in case of energy bounded orientation noise energy unbounded orientation noise existing at the same time, all array elements of the optimal orientation array are radiated by the radiation source on a given detection field. The minimum non-zero singular value $\sigma_{min}$ of the orientation matrix comprising all array elements of the optimal orientation array satisfies the relational expression:

$$\sigma_{min}=\sqrt{m/3};$$

where, m is the number of array elements constituting the orientation matrix, m≥3.

The beneficial effect of the invention is to provide a method for optimizing the performance of the existing orientation method, and lay a foundation for optimal design of non-planar array in the orientation system. The optimal orientation matrix and array provided by the invention can be used to effectively improve the orientation accuracy of the radiation source orientation system and the resistance of the orientation system to interference.

The invention is further described in combination with the drawings and the embodiments. Additional aspects and advantages of the invention are given in the following description, some of which will become apparent from the following description, or will be known through the practice of the invention.

BRIEF DESCRIPTION OF THE DRAWINGS

The drawings forming part of the application are used to provide a further understanding of the invention, and the embodiments, schematic examples and descriptions of the invention are used to explain the invention and do not constitute an improper limitation of the invention. Among the drawings.

DETAILED DESCRIPTION OF THE PREFERRED EMBODIMENTS

It should be noted that, without conflict, the embodiments and examples in the application and features thereof can be combined with each other. The invention is described in detail with reference to the drawings and in combination with the following.

In order to enable those skilled in the art to better understand the invention, the technical schemes in the embodiments and the examples are described clearly and completely in combination with the drawings in the embodiments and the examples. Apparently, the described examples are only part but not all of the examples of the invention. Based on the embodiments and examples in the invention, all other embodiments and examples obtained by those skilled in the art without creative work shall belong to the scope of protection of the invention.

The radiation source orientation determination related techniques of the invention are described below.

1. Method for Radiation Source Orientation Determination Based on Non-Planar Arrays Assuming that the rays from the radiation source to the observation point are parallel, or the distance from the radiation source to the observation point is far enough, the rays from the radiation source to the observation point are approximately parallel, such as the sunlight shining on the ground.

In order to describe the spatial direction of the radiation source and its radiation energy at the observation point, we build a vector pointing to the radiation source whose module is equal to the irradiance of the radiation source perpendicularly incident on the plane (the radiation energy per unit area of the radiated object surface), which is defined as the radiation source vector.

Figure 1:
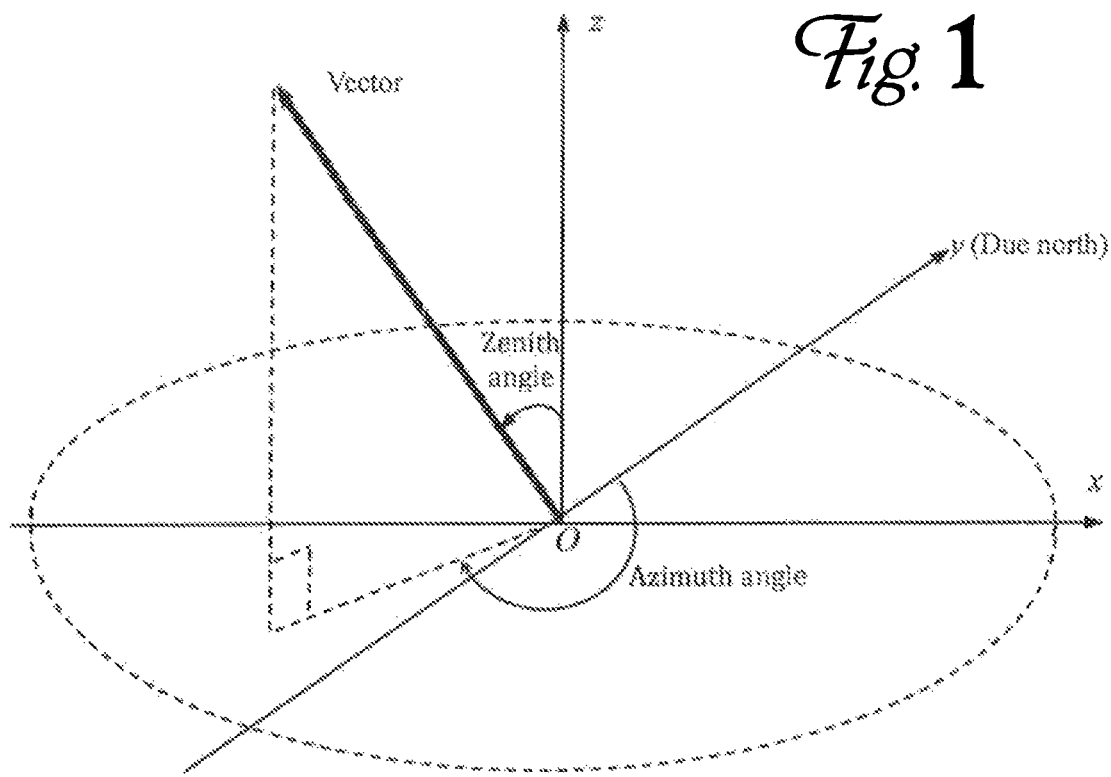
FIG. 1 is a schematic diagram illustrating zenith angle and azimuth angle of vector.

In addition, in order to describe the direction of the vector in an x-y-z Cartesian coordinate system, we define two angles for the vector: azimuth angle and zenith angle. As shown in FIG. 1, the azimuth angle of the vector is the angle from y axis clockwise rotating (or from north to east on the Earth) to the projection of the vector on x-y coordinate plane, and the zenith angle of the vector is the angle between z axis and the vector.

Figure 2:
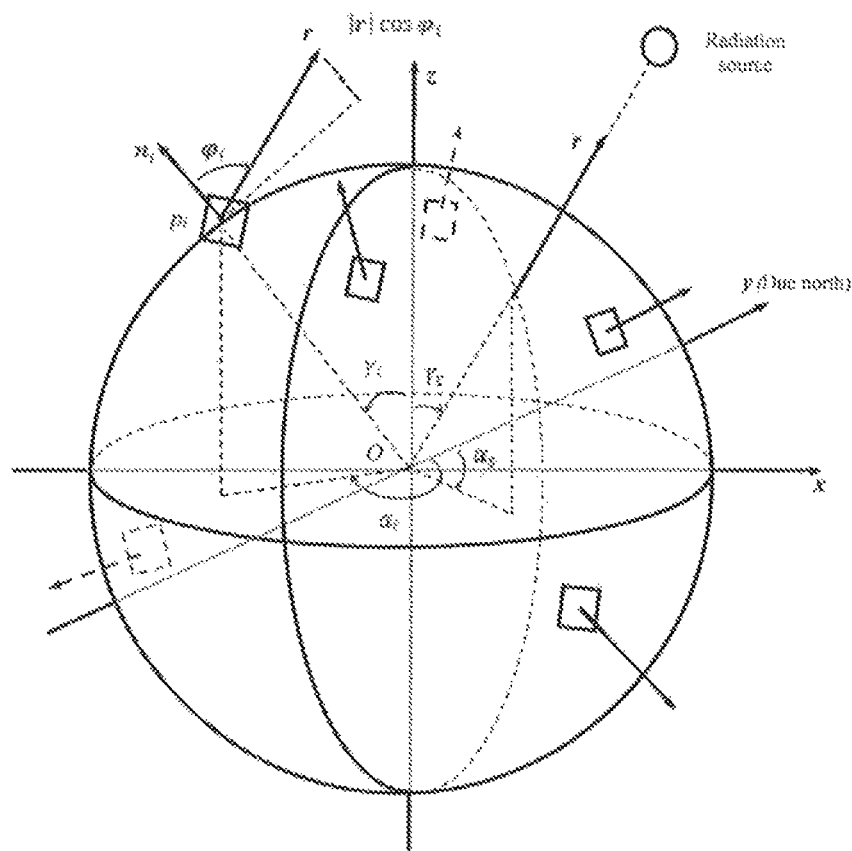
FIG. 2 is a schematic diagram illustrating the geometric relationship between the radiation source vector and the mounting plane of the array element in the radiation source orientation coordinate system.

A coordinate system for radiation source orientation determination is established with the observation point as the origin of coordinates O. In the coordinate system, the geometric relationship between the radiation source vector and the mounting plane of the array element on the non-planar array is shown in FIG. 2. In FIG. 2, the azimuth angle of the radiation source vector r is $\alpha_s$, and the zenith angle is $\gamma_s$; the azimuth angle of the unit normal vector $n_i$ of the mounting plane of the irradiated array element $p_i$ (i ∈{1,2, . . . , m}, m≥3) is $\alpha_i$, and the zenith angle is $\gamma_i$; the angle between the radiation source vector r and the unit normal vector $n_i$ is $\varphi_i$.

According to the cosine law for radiation, the irradiance of any surface varies as the cosine of the angle between the radiation energy spreading direction and the normal of the surface. According to FIG. 2, the irradiance passing through the array element $p_i$ mounting plane is $|r|\cos \varphi_i$ ($|r|$ is the irradiance of the radiation source perpendicularly incident on the array element at the observation point). Based on $|r|\cos \varphi_i = r \cdot n_i$ it can be known that the irradiance that passes through an irradiated array element is equal to the inner product of the radiation source vector and the unit normal vector on the mounting plane of the array element.

Generally, there is a transformation factor between the irradiance passing through the array element and the measured value, such as the output transformation efficiency of photodiodes or solar panels to solar radiation energy. If the transformation factor between the irradiance passing through the array element $p_i$ and the measured value $s_i$ is $\eta_i$, $s_i$ can be expressed as follows:

$$s_i = \eta_i |r| \cos \varphi_i \quad (1)$$

According to Equation (1), we can obtain the matrix equation with the radiation source vector as the unknown vector by m radiated array elements on the non-planar array:

$$\begin{pmatrix} n_1^T \\ n_2^T \\ \vdots \\ n_m^T \end{pmatrix} r = \begin{pmatrix} s_1/\eta_1 \\ s_2/\eta_2 \\ \vdots \\ s_m/\eta_m \end{pmatrix} \quad (2)$$

In Equation (2), $(n_1\ n_2\ \ldots\ n_m)^T$ consists of the unit normal vectors of m radiated array elements. In the coordinate system of radiation source orientation determination, $n_i=(\sin \alpha_i \sin \gamma_i \cos \alpha_i \sin \gamma_i \cos \gamma_i)^T$, $r=|r|(\sin \alpha_s \sin \gamma_s \cos \alpha_s \sin \gamma_s$ $\cos \gamma_s)^T$ and $|r|$ are equal to the irradiance of the radiation source perpendicularly incident on the array element.

If the rank of $(n_1\ n_2\ \ldots\ n_m)^T$ is 3, that is, the normals of mounting planes of m irradiated array elements are non-coplanar, Matrix Equation (2) has a unique solution. Assuming the coefficient matrix $(n_1\ n_2\ \ldots\ n_m)^T$ of Matrix Equation (2) is H, then:

$$H = \begin{pmatrix} \sin\alpha_1 \sin\gamma_1 & \cos\alpha_1 \sin\gamma_1 & \cos\gamma_1 \\ \sin\alpha_2 \sin\gamma_2 & \cos\alpha_2 \sin\gamma_2 & \cos\gamma_2 \\ \vdots & \vdots & \vdots \\ \sin\alpha_m \sin\gamma_m & \cos\alpha_m \sin\gamma_m & \cos\gamma_m \end{pmatrix} \quad (3)$$

Substituting Equation (3) into Equation (2), then $$Hr = \begin{pmatrix} s_1/\eta_1 \\ s_2/\eta_2 \\ \vdots \\ s_M/\eta_m \end{pmatrix} \quad (4)$$

Under an ideal condition, the same type of measuring devices are used, and the transformation factor $\eta_i$ between the irradiance passing through the array element $p_i$ and the measured value is equal to the constant $\eta$ ($\eta>0$). Therefore, Equation (4) can be simplified as:

$$H\eta r = \begin{pmatrix} s_1 \\ s_2 \\ \vdots \\ s_m \end{pmatrix} \quad (5)$$

$\eta>0$, and is in the same direction as the radiation source vector r, so the direction of the radiation source vector can be determined by solving the vector $\eta r$. Further, the irradiance that the radiation source passes through the array element is measurable. The unit normal vector of the mounting plane of the array element on the non-planar array and the coefficient matrix H are known. Thus, the direction of the radiation source vector can be obtained by solving Equation (5). Then, assuming that the measurement vector as $s=(s_1\ s_2\ \ldots\ s_m)^T$ from Equation (5), the orientation equation of the radiation source can be deducted as follows:

$$H\eta r = s \quad (6)$$

The rank of coefficient matrix H is 3, so the radiation source vector has a unique solution:

$$r = \frac{1}{\eta}(H^T H)^{-1} H^T s \quad (7)$$

Since the radiation source vector r points to the radiation source, the spatial direction of the radiation source can be determined by solving the radiation source orientation equation. According to linear OLS, the radiation source vector calculated by Equation (7) is exactly the OLS solution of the radiation source vector, and then Equation (7) is exactly also the OLS estimation equation of the radiation source vector. Therefore, we can abbreviate the above orientation method of the radiation source as the OLS orientation of the radiation source, and the coefficient matrix H of the orientation equation as the OLS orientation matrix. The invention mainly relates to the performance estimation of the orientation method and the performance optimization thereof.

In radiation source orientation equation, the OLS orientation matrix His composed of unit normal vectors of mounting plane of the radiated array elements with non-coplanar normals. Therefore, if the number of radiated elements on the non-planar array is more than 3 and their mounting planes have non-coplanar normals, it can be deducted through the array that the orientation matrix H of the OLS orientation is not unique.

2. Orientation Error of Radiation Source

In applications, the orientation system is definitely subject to the internal interference caused by the noise coming from irradiance measuring devices and misalignments of array elements, and the external interference caused by the multi-channel spreading and interfering radiation sources from surrounding environment. Due to the influence of such interference, noise must be included in the irradiance measured from the array element. For convenience of description, we define the noise included in the measured irradiance as orientation noise in Equation (7), and the disturbance vector formed by the orientation noise of the measurement vector s in Equation (7) as the orientation noise vector $\varepsilon$.

In the orientation application, due to the existence of the orientation noise vector $\varepsilon$, the OLS solution of the radiation source vector often deviates from the radiation source vector r. Assuming that the OLS solution of the radiation source vector is r', and the difference between the radiation source vector r and the OLS solution r' is the estimation error $\Delta r$ of the radiation source vector. Based on the geometric relationship between the radiation source vector r and the OLS solution r', we can define the angle between them as the orientation error $\theta$ of the radiation source.

Assuming that the radiation source vector r and its estimation error $\Delta r$ satisfy $|\Delta r|<|r|$. The geometric relationship between the radiation source orientation error $\theta$, the radiation source vector r and its OLS solution r' as well as the estimation error $\Delta r$ is shown in FIG. 3.

Figure 3:
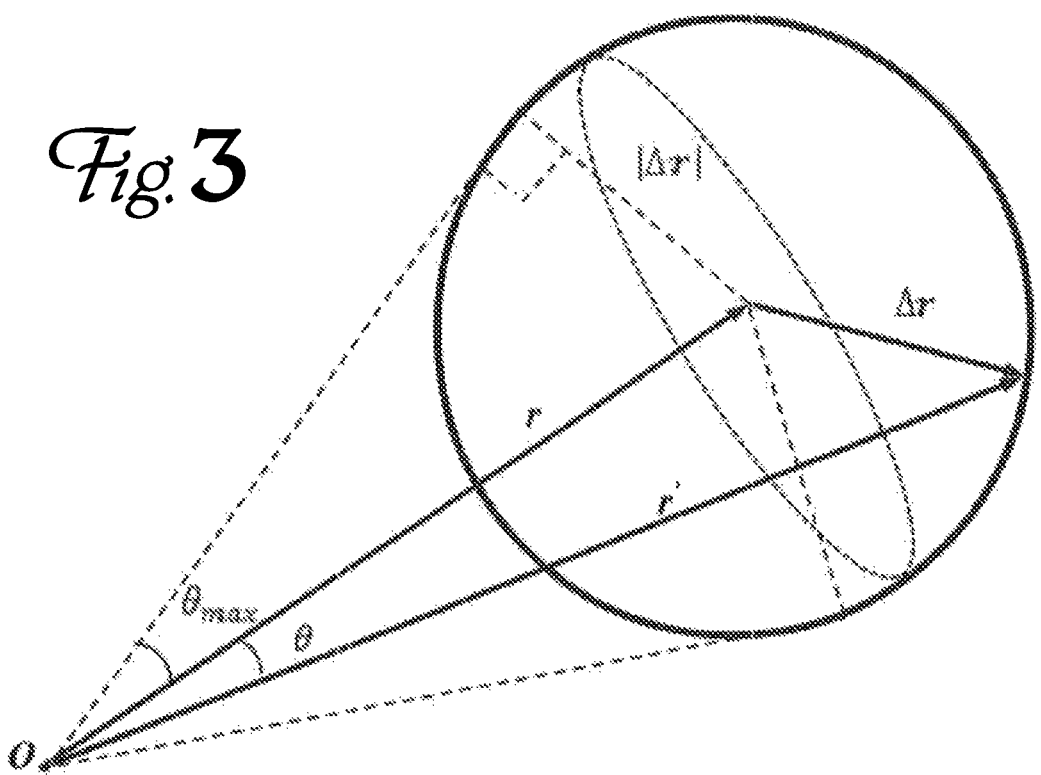
FIG. 3 is schematic diagram illustrating the geological model of orientation error of the radiation source.

It can be seen from FIG. 3 that the orientation error $\theta$ varies as the estimation error $\theta r$ of the radiation source vector. If $|\Delta r|$ remains unchanged, when the estimation error $\Delta r$ is perpendicular to the OLS solution r' of the radiation source vector, the orientation error $\theta$ reaches its maximum value $\theta_{max}$; and if the orientation error $\Delta r$ is in the same or opposite direction as the radiation source vector r, the orientation error is 0. If $|\Delta r|<|r|$ is satisfied, according to the geological relationship shown in FIG. 3, the orientation error of the radiation source can be expressed as follows:

$$\theta \leq \theta_{max} = \arcsin(|\Delta r|/|r|) \quad (8)$$

By substituting the orientation noise vector e into the least square estimation Equation (7) of the radiation source vector, the error of the radiation source vector can be estimated as follows:

$$\Delta r = \frac{1}{\eta}(H^T H)^{-1} H^T \varepsilon \quad (9)$$

Since the orientation matrix H is a column full-rank matrix of m×3, the column space of the orientation matrix is a closed subspace of the real vector space $R^m$ of m dimensions. According to the orthogonal decomposition theorem of vectors, there is a unique decomposition vector v and u for the m-dimensional orientation noise vector ε in the column space of the orientation matrix H, then ε=v+u, where v is the component vector of e projected in the column space of H and u is the component vector of e projected in the orthogonal complementary space. Since the column space of H is orthogonal to the vector u, then $H^T$ u=0. By substituting ε=v+u into the Equation (9), it can be deducted that:

$$\Delta r = \frac{1}{\eta}(H^T H)^{-1} H^T (v+u) = \frac{1}{\eta}(H^T H)^{-1} H^T v \qquad (10)$$

Comparing that Equation (9) with Equation (10) that in the OLS orientation of the radiation source, the estimation error of the radiation source vector is dependent only on the component of orientation noise vector in the orientation matrix column space, and not on the orthogonal component.

Since $\|Tx\|_2 \leq \|T\|_2 \|x\|_2$, where T is a bounded linear operator and $\|x\|_2 = |x|$ for the real vector x with the Euclidean norm, it can be deducted from Equation (10) that:

$$|\Delta r| \leq \frac{1}{\eta}\|(H^T H)^{-1} H^T\|_2 |v| \qquad (11)$$

Dividing both sides of Inequation (11) by |r|, then:

$$\frac{|\Delta r|}{|r|} \leq \|(H^T H)^{-1} H^T\|_2 \frac{|v|}{\eta|r|} \qquad (12)$$

Substituting Inequation (12) into Inequation (8), then:

$$\theta \leq \theta_{max} \leq \arcsin\left(\|(H^T H)^{-1} H^T\|_2 \frac{|v|}{\eta|r|}\right) \qquad (13)$$

According to the condition $|\Delta r| < |r|$ that holds Inequation (8), it can be deducted that $\theta_{max} < \pi/2$. Then, Inequation (13) holds on the condition of $$\|(H^T H)^{-1} H^T\|_2 \frac{|v|}{\eta|r|} < 1.$$

Generally, |v| is far smaller than η|r|. For smaller $$\|(H^T H)^{-1} H^T\|_2, \|(H^T H)^{-1} H^T\|_2 \frac{|v|}{\eta|r|} < 1$$

can be easily satisfied. Therefore, for smaller $\|(H^T H)^{-1} H^T\|_2$, Inequation (13) can be used to describe the upper bound of the minimum error of OLS orientation of the radiation source.

According to the properties of singular value, the non-zero singular value of matrix H is the positive square root of the non-zero eigenvalue of matrix $H^T H$ or $HH^T$. Similarly, the non-zero singular value of matrix $(H^T H)^{-1} H^T$ is the positive square root of non-zero eigenvalue of matrix $(H^T H)^{-1} H^T ((H^T H)^{-1} H^T)^T$. However, $(H^T H)^{-1} H^T ((H^T H)^{-1} H^T)^T = (H^T H)^{-1}$, and the eigenvalues of $(H^T H)^{-1}$ and that of $H^T H$ are the inverse of each other, which suggests that the non-zero singular values of matrix $(H^T H)^{-1} H^T$ and that of H are also the inverse of each other.

Assuming that the minimum non-zero singular value of matrix H is $\sigma_{min}$. Since the spectral norm of the matrix is equal to the maximum non-zero singular value, $\|(H^T H)^{-1} H^T\|_2 = 1/\sigma_{min}$. Generally, v is unknown, assuming $|v|^2/|\varepsilon|^2 = \mu$ and substituting $1/\sigma_{min}$ and μ into Inequation (13), the relation of error of radiation source OLS orientation can be deducted as follows:

$$\theta \leq \arcsin\left(\frac{\sqrt{\mu}}{\sigma_{min}} \frac{\sqrt{|\varepsilon|^2}}{\eta|r|}\right) \qquad (14)$$

Where, |r| is the measured irradiance of the radiation source perpendicularly incident on the array element at the observation point; η is a constant; $\sigma_{min}$ is the singular value of orientation matrix H; $|\varepsilon|^2$ is the square sum of the elements of the orientation noise vector, which is called the energy of the orientation noise; μ is the ratio of the module square $|v|^2$ of the projection vector of the orientation noise vector ε in the column space of the orientation matrix to its module square $|\varepsilon|^2$, which is determined by the orientation noise vector E and the orientation matrix H. Inequation (14) indicates that the orientation error of the radiation source is related to 3 factors: orientation noise, orientation matrix and radiation energy.

The upper bound of orientation error of the radiation source (i.e., the minimum upper bound of the orientation error) is defined as $\theta_{sup}$. It can be deducted according to Inequation (14) that the expression is as follows:

$$\theta_{sup} = \arcsin\left(\frac{\sqrt{\mu}}{\sigma_{min}} \frac{\sqrt{|\varepsilon|^2}}{\eta|r|}\right) \qquad (15)$$

In applications, the ratio μ is generally unknown. According to the Pythagorean theorem, the orientation noise vector ε and its orthogonal component vector v satisfy the inequation $|v|^2 \leq |\varepsilon|^2$. Thus, the value of μ cannot be greater than 1, that is, μ≤1. When the orientation noise vector is completely projected in the column space of the orientation matrix H, μ is the maximum value 1, and $\theta_{sup}$ is also the maximum value. Then, it can be defined that $\theta_{sup}$ of the orientation noise vector completely projected in the column space (i.e., μ=1) of orientation matrix as the maximum least upper bound $\theta_{sup\_max}$. According to Equation (15), the expression of the maximum least upper bound $\theta_{sup\_max}$ is:

$$\theta_{sup\_max} = \arcsin\left(\frac{1}{\sigma_{min}} \frac{\sqrt{|\varepsilon|^2}}{\eta|r|}\right) \qquad (16)$$

3. Method of Performance Evaluation for Radiation Source Orientation System

According to the definition of the least upper bound of orientation error of the radiation source, the performance of OLS orientation of the radiation source can be described by the least upper bound of the error of OLS orientation.

Firstly, according to the error relation $$\theta \le \arcsin\left(\frac{\sqrt{\mu}}{\sigma_{min}} \frac{\sqrt{|\varepsilon|^2}}{\eta|r|}\right)$$

of OLS orientation of the radiation source, the orientation error of the radiation source is obtained.

Secondly, the least upper bound $\theta_{sup}$ of the orientation error $\theta$ is obtained as follows:

$$\theta_{sup} = \arcsin\left(\frac{\sqrt{\mu}}{\sigma_{min}} \frac{\sqrt{|\varepsilon|^2}}{\eta|r|}\right);$$

Where, $\varepsilon$ is the orientation noise vector; $\mu$ is the ratio of the module square $|v|^2$ of the projection vector of $\varepsilon$ in the column space of the orientation matrix to its module square $|\varepsilon|^2$; $\sigma_{min}$ is the minimum non-zero singular value of the orientation matrix; $\eta$ is the transformation factor between the irradiance passing through the array element and the measured value; and r is the irradiance source vector.

Thirdly, the maximum $\theta_{sup\_max}$ is obtained through the expression of $\theta_{sup}$ as follows:

$$\theta_{sup\_max} = \arcsin\left(\frac{1}{\sigma_{min}} \frac{\sqrt{|\varepsilon|^2}}{\eta|r|}\right);$$

Then the performance of the radiation source orientation system can be determined according to $\theta_{sup\_max}$.

However, in applications, the orientation noise generated by the interference of the internal and external environment of the orientation system is usually random and unknown, which makes the projection of the orientation noise vector in the column space of the OLS orientation matrix also random and unknown.

According to the energy distribution characteristics of orientation noise, the maximum least upper bound of orientation error of the radiation source is used to indirectly evaluate the OLS orientation performance of the radiation source as follows.

A. Energy Distribution Characteristics of Orientation Noise

In applications, the radiation energy of any radiation source cannot be unbounded. According to the law of energy conservation, the energy of orientation noise generated by the interference of the internal and external environment of the orientation system can be reasonably assumed bounded on each array element.

Assume that the number of array elements constituting the OLS orientation matrix is m (m>3). For the limited m, the energy of orientation noise on each array element is bounded, and the orientation noise energy $|\varepsilon|^2$ is definitely bounded. In cases where m is big enough, the orientation noise energy $|\varepsilon|^2$ can be bounded or unbounded. However, the energy of orientation noise on each element is bounded, and then the average energy $|\varepsilon|^2/m$ of orientation noise on array element must be bounded. For example, when m→∞, the energy of orientation noise generated by failure of limited array elements is always bounded, but for uniform atmospheric scattering, the total energy $|\varepsilon|^2 \to \infty$ but the average energy $|\varepsilon|^2/m$ of orientation noise on array element is bounded because the orientation noise generated on array elements is a constant.

In conclusion, the energy of orientation noise of the radiation source can be bounded or unbounded, but the average energy of orientation noise on array element is definitely bounded. Therefore, the orientation noise of the radiation source can be classified into energy bounded noise and energy unbounded noise.

B. Method of Performance Evaluation for Orientation System Using Two Different Categories of Noise According to the categories of orientation noise of radiation source based on the above noise energy distribution characteristics, the OLS orientation performance evaluation of radiation source can be divided into: 1) performance evaluation under the scenario of orientation noise with bounded energy; 2) performance evaluation under the scenario of orientation noise with unbounded energy.

1) Performance Evaluation of Orientation System in Case of Orientation Noise with Bounded Energy According to the definition of the radiation source vector, the module $|r|$ of the radiation source vector is not only independent of the OLS orientation matrix of the radiation source, but also independent of the orientation noise. Therefore, in the error relation of OLS orientation of the radiation source, $$\theta \le \arcsin\left(\frac{\sqrt{\mu}}{\sigma_{min}} \frac{\sqrt{|\varepsilon|^2}}{\eta|r|}\right),$$

the module $|r|$ of the radiation source vector remains unchanged. Further, the transformation coefficient $\eta$ is generally a constant. Then, from Equation (16) the maximum least upper bound $\theta_{sup\_max}$ of orientation error of the radiation source is determined by the minimum non-zero singular value $\tau_{min}$ of the OLS orientation matrix under bounded $|\varepsilon|^2$, and they satisfy the relational expression:

$$\sin\theta_{sup\_max} \propto \frac{1}{\sigma_{min}} \qquad (17)$$

The interference factor of OLS orientation matrix is defined as $1/\sigma_{min}$ and marked as $\kappa$. Since $\sin \sigma_{sup\_max}$ increases monotonically with $\theta_{sup\_max}$ ($\sigma_{sup\_max}$ is within the range of $0-\pi/2$), the orientation error of the radiation source $\theta_{sup\_max}$ cannot be less than 0, it can be deducted from Equation (17) that the relationship between $\kappa$ and $\theta_{sup\_max}$ satisfies:

$$\sigma_{sup\_max} \propto \kappa \qquad (18)$$

In summary, in the scenario of orientation noise with bounded energy, the maximum upper bound of the orientation error is determined by the interference factor of the OLS orientation matrix, and they change in the same direction. In applications, since the mounting plane for the array element of the OLS orientation matrix located on the non-planar array is always known, the OLS orientation matrix is known as well. In this scenario, therefore, the OLS orientation performance of the radiation source can be evaluated via the interference factor of the OLS orientation matrix.

2) Performance Evaluation of Orientation System in Case of Orientation Noise with Unbounded Energy According to Equation (16), the maximum upper bound of orientation error of the radiation source is determined by the number of array elements m and the minimum non-zero singular value $\sigma_{min}$ under bounded $|\varepsilon|^2/m$, which satisfies the following relation:

$$\sin\theta_{sup\_max} \propto \frac{\sqrt{m}}{\sigma_{min}} \tag{19}$$

If the mean interference factor of the OLS orientation matrix is defined as $\sqrt{m}/\sigma_{min}$ and marked as $\kappa_a$. It can be deduced from Equation (19) that $\kappa_a$ and $\theta_{sup\_max}$ have the following relation:

$$\theta_{sup\_max} \propto \kappa_a \tag{20}$$

In summary, in the scenario of orientation noise with unbounded energy, the maximum upper bound of the orientation error is determined by the mean interference factor of the OLS orientation matrix, and they change in the same direction. In this scenario, meanwhile, since the OLS orientation matrix is always known, the OLS orientation performance of the radiation source can be evaluated via the mean interference factor of the OLS orientation matrix.

4. Method for Optimizing the Orientation Matrix of Radiation Source Orientation System Reducing the maximum upper bound of orientation error will improve the orientation accuracy of the radiation source on the whole. According to the above method for evaluating the performance of radiation source orientation system, the radiation source orientation noise is composed of energy bounded noise and energy unbounded noise. However, under such two kinds of noise, the maximum upper bounds of the orientation error are determined by the OLS orientation matrix. Based on this idea, the OLS orientation matrix making smaller maximum upper bound of the orientation error can be chosen to improve the orientation accuracy of the radiant source on the whole and optimize the orientation performance of the radiant source.

The method for optimizing the orientation matrix of radiation source orientation system comprises the following steps:

Step 1, establishing the radiation source orientation matrix;

Step 2, obtaining the non-zero singular value of the orientation matrix;

Step 3, determining the optimal orientation matrix of the radiation source orientation system according to the minimum non-zero singular value $\sigma_{min}$ of the orientation matrix and its number of array elements m.

According to the characteristics of orientation noise energy distribution, the orientation noise in applications can be divided into the following 3 categories:

Category 1, energy bounded noise (the square of the module of the orientation noise vector is bounded, that is, $|\varepsilon|^2$ is bounded), which is usually generated by internal interference in the orientation system;

Category 2, energy unbounded noise (the square of the module of the orientation noise vector is unbounded, but the ratio between the square of module of the orientation noise vector and the number of array elements m is bounded, that is, $|\varepsilon|^2$ is unbounded and $|\varepsilon|^2/m$ is bounded), which is usually generated by external environmental interference;

Category 3, noise mixed by energy bounded noise and energy unbounded noise.

For the above three categories of orientation noise, the performance of the OLS orientation for the radiation source can be optimized by the following methods:

When the orientation noise energy is bounded, the minimum interference factor K of the OLS orientation matrix should be taken into account, and the optimal orientation matrix should be selected to minimize the maximum upper bound of orientation error of the radiation source.

That is to say, in the case of such interference, among all the orientation matrices of the radiation source orientation system, the orientation matrix with the largest minimum non-zero singular value $\sigma_{min}$ should be taken as the optimal orientation matrix.

When the orientation noise energy is unbounded, the minimum mean interference factor $\kappa_a$ of the OLS orientation matrix should be taken into account, and the optimal orientation matrix should be selected to minimize the maximum upper bound of orientation error of the radiation source;

That is to say, in the case of such interference, among all the orientation matrices of the radiation source orientation system, the matrix with the minimum $\sqrt{m}/\sigma_{min}$ should be taken as the optimal orientation matrix.

In case that energy bounded orientation noise and energy unbounded orientation noise exists at the same time, because it is composed of Category 1 and Category 2 orientation noise, the OLS orientation matrix with minimum interference factor κ and minimum mean interference factor $\kappa_a$ should be taken into account, and the optimal orientation matrix should be selected to minimize the maximum upper bound of orientation error of the radiation source. That is to say, the orientation matrix with both minimum interference factor κ and minimum mean interference factor $\kappa_a$ should be taken as the optimal orientation matrix.

According to the above optimization criteria for the optimal orientation matrix, the optimal orientation matrix of Category 3 orientation noise is not only that of Category 1 orientation noise, but also that of Category 2 as well. Therefore, it is suitable for optimizing the OLS orientation performance of the radiation source under any orientation noise.

A. Selection of the Optimal Orientation Matrix

As defined to OLS orientation matrix H, it is composed of unit normal vectors of mounting plane of m array elements on the orientation array, which is a m×3 column full rank matrix. According to the properties of singular value, the trace of matrix $H^T H$ is equal to the sum of squares of the singular value of orientation matrix H and at the same time, the trace of $H^T H$ is equal to m. It can be deduced that the sum of squares of the singular value of orientation matrix H is equal to m. Considering the number of non-zero singular values for the column full rank orientation matrix H is 3 and their sum of squares is m, its minimum non-zero singular value $\sigma_{min}$ should meet the inequation:

$$\sigma_{min} \le \sqrt{m/3} \tag{21}$$

Where, when the orientation matrix H has equal non-zero singular values, $\sigma_{min} = \sqrt{m/3}$.

As defined to the interference factor K of OLS orientation matrix, it can be deduced from Inequation (21) that:

$$\kappa = 1/\sigma_{min} \le \sqrt{3}/\sqrt{m} \tag{22}$$

Inequation (22) indicates that, if the number of array elements for orientation matrix is given, κ has a minimum value which can be determined. In applications, the number of array elements for orientation array is certain, and the OLS orientation matrix is composed of unit normal vectors of mounting plane of array elements on the orientation array. Therefore, the maximum number of array elements constituting OLS orientation matrix is also certain, and correspondingly, the interference factor has a minimum value which can be determined. Then, if the number of array elements constituting the orientation matrix is given, it can be defined that the minimum interference factor κ of OLS orientation matrix is $\kappa_{min}$.

Assuming that the orientation matrix H has equal non-zero singular values, namely $\sigma_{min}=\sqrt{m/3}$, it can be deduced from Inequation (22) that:

$$\kappa_{min}=\sqrt{3}/\sqrt{m} \qquad (23)$$

Similarly, if $\kappa_{a\_min}$ is defined as the minimum value for the mean interference factor $\kappa_a$ of OLS orientation matrix, it can be deduced from Equation (23), according to the relation between the interference factor κ and the mean interference factor $\kappa_a$, that:

$$\kappa_{a\_min}=\sqrt{m}\kappa_{min}=\sqrt{3} \qquad (24)$$

When the OLS orientation matrix has equal non-zero singular values, it can be deduced from Equations (23) and (24) that the interference factor κ and the mean interference factor $\kappa_a$ are both at the minimum. From the criteria for selecting the optimal orientation matrix, it can be deduced that, regardless of any orientation noise energy distribution, the optimal OLS orientation matrix at radiation source orientation determination meets the basic characteristic of equal non-zero singular values.

B. Method for Optimizing the Orientation Array of Radiation Source Orientation System The optimal orientation array is determined according to the non-zero singular value of orientation matrix considering the characteristics of different energy distribution of the orientation noise in the radiation source orientation system.

According to the method for optimizing the orientation matrix of radiation source orientation system, the performance of radiation source OLS orientation can be optimized by its optimal orientation matrix. However, as defined to OLS orientation matrix, its optimal orientation matrix is composed of unit normal vectors of mounting plane of array elements. Therefore, optimizing the OLS orientation performance of the radiation source means optimizing the structure design of orientation array first.

In applications, the maximum number of available array elements for orientation array can be determined because of bounded number of array elements for radiation source orientation arrays. Assuming that the designed number of array elements for the orientation array is m, since the number of array elements constituting OLS orientation matrix cannot be greater than the total number of array elements, there is no OLS orientation matrix with the number of array elements greater than m in the array.

Then, it can be seen from Equation (23) that, in order to obtain the optimal orientation matrix in the context of energy bounded orientation noise, that is, the orientation matrix where interference factor equals to the minimum value $\sqrt{3}/\sqrt{m}$, the structure of such array should meet the following requirements:

(1) Among all the orientation matrices formed by array elements of this array, there is an orientation matrix where the number of array elements is m, namely all array elements of this orientation array are irradiated by the radiation source;

(2) The orientation matrix whose number of array elements is m has equal non-zero singular values.

Similarly, it can be seen from Equation (24) that, when an OLS orientation matrix has equal non-zero singular values, its minimum mean interference factor is a constant $\sqrt{3}$, which is independent of the number of array elements constituting orientation matrix. Therefore, for any matrix satisfying the basic characteristics of the optimal orientation matrix for radiation source OLS orientation, its mean interference factor should be the minimum value $\sqrt{3}$. It can be deduced that, in order to obtain the optimal orientation matrix with energy unbounded orientation noise, the structure of such array should meet the following requirements:

(1) Among all the orientation matrices formed by array elements of this array, there is an orientation matrix with equal non-zero singular values.

By comparing the structure of realized array of optimal orientation matrices under the condition of energy bounded orientation noise and energy unbounded orientation noise, it can be seen that the realized array of the former optimal orientation matrix must be exactly that of the latter optimal orientation matrix. In addition, according to the criteria for selecting optimal orientation matrix for Category 3 orientation noise, the optimal orientation matrix for Category 3 orientation noise must be that for Category 1 and Category 2 orientation noise. It can be deduced that, if the maximum upper bound of orientation error of the radiation source is at the minimum, the realized array of the optimal orientation matrix with orientation noise of any energy distribution can be designed as per the following criteria:

(1) In the given detection field, all array elements are irradiated by radiation source;

(2) The orientation matrix composed of all array elements has equal non-zero singular values.

We claim:

1. Method for optimizing the orientation performance of radiation source orientation system, characterized in comprising the following steps:

Establishing a radiation source orientation matrix;

Obtaining a non-zero singular value of the radiation source orientation matrix;

Classifying an orientation noise that affects the radiation source orientation system according to a distribution characteristic of noise energy;

Determining an optimal orientation matrix of the radiation source orientation system according to the minimum non-zero singular value $\sigma_{min}$ of the orientation matrix and its number of array elements m;

Determining an optimal orientation array is according to the non-zero singular value of the radiation source orientation matrix considering the different noise energy distribution, and further characterized in that, in case of energy bounded orientation noise, among all orientation matrices of the radiation source orientation system, an orientation matrix with a largest minimum non-zero singular value $\sigma_{min}$ is taken as the optimal orientation array.

2. The method for optimizing the orientation performance of radiation source orientation system according to claim 1, characterized in that, in case of energy bounded orientation noise, all array elements of the optimal orientation array are radiated by a radiation source on a given detection field; the minimum non-zero singular value $\sigma_{min}$ of the orientation matrix comprising all array elements of the optimal orientation array satisfies a relational expression:

$$\sigma_{min} \leq \sqrt{m/3};$$

where, m is a number of array elements constituting the orientation matrix, m≥3.

3. The method for optimizing the orientation performance of radiation source orientation system according to claim 1, characterized in that, in case of energy unbounded orientation noise, among all orientation matrices comprising a radiated array elements of the optimal orientation array, there is at least one orientation matrix with a minimum non-zero singular value $\sigma_{min}$ satisfying a relational expression:

$$\sigma_{min} \leq \sqrt{m/3};$$

where, m is a number of array elements constituting the orientation matrix, m≥3.

4. The method for optimizing the orientation performance of radiation source orientation system according to claim 1, characterized in that, in case of energy bounded orientation noise and energy unbounded orientation noise, all array elements of the optimal orientation array are radiated by a radiation source on a given detection field; a minimum non-zero singular value $\sigma_{min}$ of the orientation matrix comprising all array elements of the optimal orientation array satisfies a relational expression:

$$\sigma_{min} \leq \sqrt{m/3};$$

where, m is a number of array elements constituting the orientation matrix, m≥3.

5. Method for optimizing the orientation performance of radiation source orientation system, characterized in comprising the following steps:
Establishing a radiation source orientation matrix;
Obtaining a non-zero singular value of the radiation source orientation matrix;
Classifying an orientation noise that affects the radiation source orientation system according to a distribution characteristic of noise energy;
Determining an optimal orientation matrix of the radiation source orientation system according to the minimum non-zero singular value $\sigma_{min}$ of the orientation matrix and its number of array elements m;
Determining an optimal orientation array is according to the non-zero singular value of the radiation source orientation matrix considering the different noise energy distribution,
and further characterized in that in case of energy unbounded orientation noise, among all orientation matrices of the radiation source orientation system, an orientation matrix with a minimum $\sqrt{m/\sigma_{min}}$ is taken as the optimal orientation array.

6. The method for optimizing the orientation performance of radiation source orientation system according to claim 5, characterized in that, in case of energy bounded orientation noise, all array elements of the optimal orientation array are radiated by a radiation source on a given detection field; the minimum non-zero singular value $\sigma_{min}$ of the orientation matrix comprising all array elements of the optimal orientation array satisfies a relational expression:

$$\sigma_{min} \leq \sqrt{m/3};$$

where, m is a number of array elements constituting the orientation matrix, m≥3.

7. The method for optimizing the orientation performance of radiation source orientation system according to claim 5, characterized in that, in case of energy unbounded orientation noise, among all orientation matrices comprising a radiated array elements of the optimal orientation array, there is at least one orientation matrix with a minimum non-zero singular value $\sigma_{min}$ satisfying a relational expression:

$$\sigma_{min} \leq \sqrt{m/3};$$

where, m is a number of array elements constituting the orientation matrix, m≥3.

8. The method for optimizing the orientation performance of radiation source orientation system according to claim 5, characterized in that, in case of energy bounded orientation noise and energy unbounded orientation noise, all array elements of the optimal orientation array are radiated by a radiation source on a given detection field; a minimum non-zero singular value $\sigma_{min}$ of the orientation matrix comprising all array elements of the optimal orientation array satisfies a relational expression:

$$\sigma_{min} \leq \sqrt{m/3};$$

where, m is a number of array elements constituting the orientation matrix, m≥3.

9. Method for optimizing the orientation performance of radiation source orientation system, characterized in comprising the following steps:
Establishing a radiation source orientation matrix;
Obtaining a non-zero singular value of the radiation source orientation matrix;
Classifying an orientation noise that affects the radiation source orientation system according to a distribution characteristic of noise energy;
Determining an optimal orientation matrix of the radiation source orientation system according to the minimum non-zero singular value $\sigma_{min}$ of the orientation matrix and its number of array elements m;
Determining an optimal orientation array is according to the non-zero singular value of the radiation source orientation matrix considering the different noise energy distribution,
and further characterized in that, in case of energy bounded orientation noise and energy unbounded orientation noise, an orientation matrix with a minimum interference factor K and a minimum mean interference factor $\kappa_\alpha$ is taken as the optimal orientation matrix;
where, $\kappa = 1/\sigma_{min}$, $\kappa_{60} = \sqrt{m}/\sigma_{min}$; m is a number of array elements constituting the orientation matrix, m≥3.

10. The method for optimizing the orientation performance of radiation source orientation system according to claim 9, characterized in that, in case of energy bounded orientation noise, all array elements of the optimal orientation array are radiated by a radiation source on a given detection field; the minimum non-zero singular value $\sigma_{min}$ of the orientation matrix comprising all array elements of the optimal orientation array satisfies a relational expression:

$$\sigma_{min} \leq \sqrt{m/3};$$

where, m is a number of array elements constituting the orientation matrix, m≥3.

11. The method for optimizing the orientation performance of radiation source orientation system according to claim 9, characterized in that, in case of energy unbounded orientation noise, among all orientation matrices comprising a radiated array elements of the optimal orientation array, there is at least one orientation matrix with a minimum non-zero singular value $\sigma_{min}$ satisfying a relational expression:

$$\sigma_{min} \leq \sqrt{m/3};$$

where, m is a number of array elements constituting the orientation matrix, m≥3.

12. The method for optimizing the orientation performance of radiation source orientation system according to claim 9, characterized in that, in case of energy bounded orientation noise and energy unbounded orientation noise, all array elements of the optimal orientation array are radiated by a radiation source on a given detection field; a minimum non-zero singular value $\sigma_{min}$ of the orientation matrix comprising all array elements of the optimal orientation array satisfies a relational expression:

$$\sigma_{min} \leq \sqrt{m/3}; \qquad (5)$$

where, m is a number of array elements constituting the orientation matrix, $m \geq 3$.

* * * * *